United States Patent
Ueki et al.

(10) Patent No.: US 6,998,477 B1
(45) Date of Patent: Feb. 14, 2006

(54) NUCLEIC ACID FRAGMENT, RECOMBINANT VECTOR CONTAINING THE SAME AND METHOD OF PROMOTING THE EXPRESSION OF STRUCTURAL GENES BY USING THE SAME

(75) Inventors: Jun Ueki, Shizuoka (JP); Shinji Morioka, Shizuoka (JP)

(73) Assignee: Japan Tobacco Inc., Tokyo (JP)

( * ) Notice: Subject to any disclaimer, the term of this patent is extended or adjusted under 35 U.S.C. 154(b) by 153 days.

(21) Appl. No.: 09/856,725

(22) PCT Filed: Sep. 25, 2000

(86) PCT No.: PCT/JP00/06560

§ 371 (c)(1),
(2), (4) Date: May 25, 2001

(87) PCT Pub. No.: WO01/23544

PCT Pub. Date: Apr. 5, 2001

(30) Foreign Application Priority Data

Sep. 27, 1999 (JP) ................................. 27176299

(51) Int. Cl.
*C12N 15/63* (2006.01)
*C12N 15/67* (2006.01)
*C12N 15/82* (2006.01)
*A01H 5/00* (2006.01)

(52) U.S. Cl. .................... 536/24.1; 536/23.1; 800/278; 800/298; 435/320.1

(58) Field of Classification Search ............ 435/320.1, 435/419, 468; 536/24.1; 800/278, 298
See application file for complete search history.

(56) References Cited

U.S. PATENT DOCUMENTS 5,747,327 A   5/1998   Ueki et al.
5,801,016 A   9/1998   Morioka et al.
5,973,226 A  10/1999   Ueki et al.

FOREIGN PATENT DOCUMENTS

EP   0 685 559 A1   12/1995
EP   0846770        6/1998
EP   1050580       11/2000

OTHER PUBLICATIONS

Fourgoux-Nicol et al. 1999, Plant Molecular Biology 40 : 857-872.*
Benfey et al., Science 250:959-966, 1990.*
Izawa T. et al., J. Mol. Biol., 1993; vol. 230; pp. 1131-1144.*
Ueki J. et al., Plant Cell and Physiology, Jun. 1999; vol. 40, No. 6; pp. 618-623.*
Tanaka A. et al. Nucleic Acids Research, 1990; vol. 18, No. 23, pp. 6767-6770.*
Mascarenhas et al., "Intron-Mediated Enhancement Of Heterologous Gene Expression In Maize", *Plant Molecular Biology*, vol. 15, pp. 913-920, 1990.
Clancy et al., "Maize Shrunken-1 Intron and Exon Regions Increase Gene Expression In Maize Protoplasts", *Plant Science*, vol. 98, pp. 151-161, 1994.
Callis et al., "Introns Increase Gene Expression In Cultured Maize Cells", *Genes & Development*, vol. 1, pp. 1183-1200, 1987.
Simpson et al., "Splicing of Precursors to mRNA in Higher Plants: Mechanism, Regulation and Sub-nuclear Organisation of the Splicesomal Machinery", *Plant Molecular Biology*, vol. 32, pp. 1-41, 1996.
EMBL Online; Mar. 22, 1997; database accession No. OSAB1920; XP002280927.

* cited by examiner

*Primary Examiner*—Phuong T. Bui
*Assistant Examiner*—Russell Kallis
(74) *Attorney, Agent, or Firm*—Birch, Stewart, Kolasch & Birch, LLP

(57) ABSTRACT

A novel nucleic acid fragment which has an high activity to promote expression of a structural gene located downstream thereof, and a method for promoting expression of the structural gene located downstream thereof using the nucleic acid are disclosed. A nucleic acid fragment having the nucleotide sequence shown in SEQ ID NO:1 in the Sequence Listing, and nucleic acid fragments having the same sequence as shown in SEQ ID NO:1 except that one or more nucleotides are substituted or deleted, or one or more nucleotides are inserted therein or added thereto, which have activities to promote expression of a structural gene located downstream thereof were provided.

7 Claims, No Drawings

US 6,998,477 B1

NUCLEIC ACID FRAGMENT, RECOMBINANT VECTOR CONTAINING THE SAME AND METHOD OF PROMOTING THE EXPRESSION OF STRUCTURAL GENES BY USING THE SAME

This is application is the national phase under 35 U.S.C. § 371 of PCT International Application No. PCT/JP00/06560 which has an International filing date of Sep. 25, 2000, which designated the United States of America and was published in Japanese.

TECHNICAL FIELD

The present invention relates to a nucleic acid fragment having an activity to promote expression of a structural gene located at a downstream site thereof, a recombinant vector containing the same, and to a method for expressing the structural gene using the same, as well as to a plant in which expression of a desired structural gene is promoted by the method.

BACKGROUND ART

Promotion of foreign gene expression is the most required technique in applying the genetic engineering technique to plants. One of the techniques is the utilization of DNA fragments. Known DNA fragments which promote expression of foreign genes include some introns (Simpson and Filipowicz 1996. Plant Mol. Biol. 32: 1–41) including an intron of maize alcohol dehydrogenase (Callis et al. Gene & Development 1, 1183–1200 (1987)), as well as the first intron of rice phospholipase D (WO96/30510). Influences of deletion of apart of inner regions of DNA fragments derived from introns, and of insertion of the same intron into the intron, on the promotion of expression have been reported (Mascarenhas et al. Plant Mol. Biol. 15, 913–920 (1990), Clancy et al. Plant Sci. 98, 151–161 (1994)).

However, so far, types of available DNA fragments are limited. Further, actions of the DNA fragments vary depending on the type of the plant, and vary depending on the organs or tissues even in the same plant (Simpson and Filipowicz 1996. Plant Mol. Biol. 32: 1–41). Therefore, existence of DNA fragments exhibiting various types of expression-promotion actions is desired.

DISCLOSURE OF THE INVENTION

Accordingly, an object of the present invention is to provide a novel nucleic acid fragment having an activity to promote expression of a structural gene located downstream thereof, and to provide a method for promoting expression of the structural gene downstream thereof.

The present inventors intensively studied to discover that the second intron of rice PLD gene has a high activity to promote gene expression, thereby completing the present invention.

That is, the present invention provides a nucleic acid fragment having the nucleotide sequence shown in SEQ ID NO:1 in the Sequence Listing, or having the same nucleotide sequence as shown in SEQ ID NO:1 except that one or more nucleotides are substituted or deleted, or one or more nucleotides are inserted therein or added thereto, which has an activity to promote expression of a structural gene located downstream thereof. The present invention also provides a nucleic acid fragment having the nucleotide sequence shown in SEQ ID NO:1 in the Sequence Listing, or a nucleic acid fragment which hybridizes with the nucleic acid fragment under stringent conditions, which has an activity to promote expression of a structural gene located downstream thereof. The present invention further provides a recombinant vector which contains the above-described nucleic acid fragment according to the present invention and a structural gene located downstream of the nucleic acid fragment, by which expression of the structural gene is promoted by the nucleic acid fragment. The present invention further provides a method for promoting expression of a structural gene comprising inserting the nucleic acid fragment according to the present invention into a site upstream of the structural gene. The present invention further provides a plant in which expression of a desired structural gene is promoted, and progenies thereof retaining the character.

By the present invention, a novel nucleic acid fragment having a high activity to promote expression of a structural gene was provided. As is apparent from the Example below, the activity of the nucleic acid fragment according to the present invention to promote expression of the structural gene downstream thereof is much larger than that of the known first intron of rice PLD gene, which has the similar function. Therefore, by inserting the nucleic acid fragment of the present invention into a site upstream of the structural gene, expression of the structural gene is much more promoted. Thus, by the present invention, for example, expression of a foreign gene using a recombinant vector may be much more promoted, so that the present invention will make a large contribution in the field of genetic engineering.

BEST MODE FOR CARRYING OUT THE INVENTION

As mentioned above, the nucleic acid fragment according to the present invention is a nucleic acid fragment having the nucleotide sequence shown in SEQ ID NO:1 in the Sequence Listing, or having the same sequence as shown in SEQ ID NO:1 except that one or more nucleotides are substituted or deleted, or one or more nucleotides are inserted therein or added thereto, which has an activity to promote expression of a structural gene located downstream thereof.

As mentioned above, the nucleic acid fragments (hereinafter also referred to as "modified nucleic acid fragment" for convenience) having the same nucleotide sequence as shown in SEQ ID NO: 1 except that one or a plurality of nucleotides are substituted or deleted, or except that one or a plurality of nucleotides are inserted or added, which have activities to promote expression of a structural gene located downstream of the nucleic acid fragments are also within the scope of the present invention. In this case, the region in the modified nucleic acid fragment, which corresponds to a region in the sequence shown in SEQ ID NO:1 preferably has a homology of not less than 70%, more preferably not less than 85%, more preferably not less than 95% with the sequence shown in SEQ ID NO:1. The homology of the nucleotide sequence may easily be calculated by using a well-known software such as FASTA. Further, these modified nucleic acid fragments preferably hybridize with the nucleic acid having the nucleotide sequence shown in SEQ ID NO: 1 under stringent conditions (i.e., hybridization is carried out in an ordinary hybridization solution such as 5×Denhardt's reagent, 6×SSC, 0.5% SDS or 0.1% SDS, at 50 to 65° C., preferably in two steps at 50° C. and at 60° C., or in four steps at 50° C., 55° C., 60° C. and 65° C.).

The nucleic acid fragments each of which is a part of the nucleic acid fragment having the nucleotide sequence shown in SEQ ID NO:1, which have activities to promote expression of a structural gene located downstream of the nucleic acid fragments are also within the scope of the present invention. Further, nucleic acid fragments obtained by ligating a plurality of the nucleic acid fragments according to the present invention are also within the scope of the present invention. In this case, the nucleic acid fragments according to the present invention may be directly ligated or an intervening sequence may exist therebetween.

The nucleic acid according to the present invention may be either DNA or RNA. However, DNA is preferred in view of stability.

Since the nucleotide sequence of the nucleic acid fragment according to the present invention has been determined by the present invention and since the nucleic acid fragment is originated from the genome of rice, the nucleic acid fragment may easily be prepared by a nucleic acid-amplification method such as PCR using the genomic DNA of rice as the template. PCR is well-known in the art and a kit and apparatus therefor are commercially available, so that it can be easily carried out. Further, the above-mentioned modified nucleic acid fragments may be obtained by subjecting the thus obtained nucleic acid fragment to the well-known site-specific mutagenesis.

In cases where a plurality of nucleic acid fragments according to the present invention are ligated, a plurality of nucleic acid fragments according to the present invention may be preliminarily ligated, or a nucleic acid fragment according to the present invention may be inserted into a region containing the nucleic acid fragment according to the present invention.

By inserting the above-described nucleic acid fragment according to the present invention to a site upstream of a structural gene, the expression of the structural gene may be promoted. Structural genes are controlled by a promoter located upstream thereof. The nucleic acid fragment according to the present invention may be inserted either between the promoter and the structural gene or at a site upstream of the promoter, and the former is preferred. In this case, the distance between the nucleic acid fragment according to the present invention and the structural gene may preferably be 0 bp to 1000 bp, and the distance between the promoter and the nucleic acid fragment according to the present invention may also preferably be 0 bp to 1000 bp.

The present invention also provides recombinant vectors obtained by applying the above-described method of the present invention to an expression vector. The recombinant vector according to the present invention may easily be prepared by inserting the nucleic acid fragment according to the present invention and a structural gene of which expression is to be promoted into a cloning site of a commercially available expression vector. Such an expression vector may preferably be one for plants. Various expression vectors for plants are well-known in the art and commercially available.

These expression vectors include a replication origin for replication in host cells, a promoter, cloning sites giving restriction sites for inserting foreign genes, and a selection marker such as a drug resistant gene, and usually contain a terminator which stably terminates transcription. In the method of the present invention, any of these known expression vectors may be employed.

EXAMPLE

The present invention will now be described more concretely by way of examples thereof. It should be noted that the present invention is not restricted to the Example.

A DNA fragment having the second intron of rice PLD gene and 37mer exon regions at both ends of the second intron (the nucleotide of this DNA fragment is shown in SEQ ID NO:2 in Sequence Listing) was amplified by PCR using the following primers and a known rice genomic clone (SEQ ID NO:5 of WO95/0934) as the template.

5'-aagtcccccg ggccgcgcca gcggaag-3' (SEQ ID NO: 4)
3'-gacacccaca gccgtctata gttcgta-5' (SEQ ID NO: 6)

The obtained fragments amplified by PCR were digested with Sma I and Eco RV and inserted into the Sma I site of a vector pBI221 commercially available from CLONTECH, which contains a β-glucuronidase (GUS) gene at a downstream site of 35S promoter. Transient expression of the gene was examined by the method of Sheen (Sheen 1991, Plant Cell 3:225–245). That is, the constructed plasmids were introduced into protoplasts isolated from etiolated maize leaves by electroporation, and transient expression of GUS was measured by the above-mentioned method.

For comparison, the first intron (SEQ ID NO:3 in Sequence Listing) of rice PLD gene was amplified by PCR by the method described in WO96/30510 and inserted into the Sma I site of pBI221, followed by introduction of the obtained vector into maize in the similar manner as described above. The expression of GUS was determined. The results are shown in Table 1 below.

TABLE 1

| Plasmid | GUS Activity (4-MU pmol/$10^7$ cells/min) |
|---|---|
| pBI221 (35S promoter, GUS) (Comparative Example) | 140 |
| pBI221 + PLD first intron (Comparative Example) | 630 |
| pBI221 + PLD second intron (Example) | 11,000 |

As is apparent from these results, the activity of the nucleic acid fragment according to the present invention to promote expression of the structural gene located downstream thereof is much higher than that of the first intron of rice PLD, which is known to have the similar function.

What is claimed is:

1. An isolated nucleic acid comprising SEQ ID NO: 1.

2. An isolated nucleic acid comprising SEQ ID NO: 2.

3. A recombinant vector comprising the nucleic acid according to any one of claims 1 or 2, and a polynucleotide encoding a protein of interest located downstream of said nucleic acid, wherein said nucleic acid is operably linked to said polynucleotide and promotes expression of said polynucleotide.

4. A method for expressing a polynucleotide encoding a protein of interest comprising, inserting the nucleic acid according to any one of claims 1 or 2 into a site upstream of said polynucleotide, wherein said nucleic acid is operably linked to said polynucleotide and promotes expression of said polynucleotide, and expressing said polynucleotide encoding said protein of interest.

5. A transgenic plant comprising the nucleic acid according to any one of claims 1 or 2, whereby said nucleic acid is operably linked to and expresses a polynucleotide encoding a protein of interest.

6. The method according to claim 4, wherein the nucleic acid is inserted into a site 0 base pairs to 1000 base pairs upstream from the polynucleotide encoding a protein of interest.

7. A plant comprising the recombinant vector according to claim 3, or a progeny of said plant, wherein the progeny comprises the recombinant vector according to claim 3.

* * * * *

SEQUENCE LISTING (1) GENERAL INFORMATION:

(iii) NUMBER OF SEQUENCES: 16

(2) INFORMATION FOR SEQ ID NO:1:

-continued (i) SEQUENCE CHARACTERISTICS:
    (A) LENGTH: 423 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:1:

```
Met Ser Asp Ser Lys Ser Asp Gly Gln Phe Tyr Ser Val Gln Val Ala
  1               5                  10                  15

Asp Ser Thr Phe Thr Val Leu Lys Arg Tyr Gln Gln Leu Lys Pro Ile
             20                  25                  30

Gly Ser Gly Ala Gln Gly Ile Val Cys Ala Ala Phe Asp Thr Val Leu
         35                  40                  45

Gly Ile Asn Val Ala Val Lys Lys Leu Ser Arg Pro Phe Gln Asn Gln
     50                  55                  60

Thr His Ala Lys Arg Ala Tyr Arg Glu Leu Val Leu Leu Lys Cys Val
 65                  70                  75                  80

Asn His Lys Asn Ile Ile Ser Leu Leu Asn Val Phe Thr Pro Gln Lys
                 85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Ala Glu Met Val Leu His Lys Ser Cys
210                 215                 220

Ser Pro Gly Arg Asp Tyr Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
        355                 360                 365
```

```
Asn Gly Val Lys Asp Gln Pro Ser Asp Ala Ala Val Ser Ser Lys Ala
    370                 375                 380

Thr Pro Ser Gln Ser Ser Ser Ile Asn Asp Ile Ser Ser Met Ser Thr
385                 390                 395                 400

Glu His Thr Leu Ala Ser Asp Thr Asp Ser Ser Leu Asp Ala Ser Thr
                405                 410                 415

Gly Pro Leu Glu Gly Cys Arg
            420
```

(2) INFORMATION FOR SEQ ID NO:2:

(i) SEQUENCE CHARACTERISTICS:
        (A) LENGTH: 423 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ser Asp Ser Lys Ser Asp Gly Gln Phe Tyr Ser Val Gln Val Ala
1                   5                   10                  15

Asp Ser Thr Phe Thr Val Leu Lys Arg Tyr Gln Gln Leu Lys Pro Ile
                20                  25                  30

Gly Ser Gly Ala Gln Gly Ile Val Cys Ala Ala Phe Asp Thr Val Leu
                35                  40                  45

Gly Ile Asn Val Ala Val Lys Lys Leu Ser Arg Pro Phe Gln Asn Gln
            50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                    85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
            195                 200                 205

Trp Ser Val Gly Cys Ile Met Gly Glu Leu Val Lys Gly Cys Val Ile
        210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
                260                 265                 270

Glu Leu Phe Pro Asp Trp Ile Phe Pro Ser Glu Ser Glu Arg Asp Lys
            275                 280                 285
```

-continued

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
                340                 345                 350

Lys Glu Leu Ile Tyr Lys Glu Val Met Asp Trp Glu Glu Arg Ser Lys
                355                 360                 365

Asn Gly Val Lys Asp Gln Pro Ser Asp Ala Ala Val Ser Ser Lys Ala
    370                 375                 380

Thr Pro Ser Gln Ser Ser Ser Ile Asn Asp Ile Ser Ser Met Ser Thr
385                 390                 395                 400

Glu His Thr Leu Ala Ser Asp Thr Asp Ser Ser Leu Asp Ala Ser Thr
                405                 410                 415

Gly Pro Leu Glu Gly Cys Arg
                420

(2) INFORMATION FOR SEQ ID NO:3:

(i) SEQUENCE CHARACTERISTICS:
        (A) LENGTH: 426 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Ser Lys Ser Lys Val Asp Asn Gln Phe Tyr Ser Val Glu Val Gly
1               5                   10                  15

Asp Ser Thr Phe Thr Val Leu Lys Arg Tyr Gln Asn Leu Lys Pro Ile
                20                  25                  30

Gly Ser Gly Ala Gln Gly Ile Val Cys Ala Ala Tyr Asp Ala Val Leu
            35                  40                  45

Asp Arg Asn Val Ala Ile Lys Lys Leu Ser Arg Pro Phe Gln Asn Gln
        50                  55                  60

Thr His Ala Lys Arg Ala Tyr Arg Glu Leu Val Leu Met Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
                100                 105                 110

Ala Asn Leu Cys Gln Val Ile Gln Met Glu Leu Asp His Glu Arg Met
            115                 120                 125

Ser Tyr Leu Leu Tyr Gln Met Leu Ser Ala Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
            195                 200                 205

-continued

```
Trp Ser Val Gly Cys Ile Met Gly Glu Met Val Arg His Lys Ile Leu
    210                 215                 220
Phe Pro Gly Arg Asp Tyr Ile Asp Gln Trp Asn Lys Val Ile Glu Gln
225                 230                 235                 240
Leu Gly Thr Pro Cys Pro Glu Phe Met Lys Lys Leu Gln Pro Thr Val
                245                 250                 255
Arg Asn Tyr Val Glu Asn Arg Pro Lys Tyr Ala Gly Leu Thr Phe Pro
            260                 265                 270
Lys Leu Phe Pro Asp Ser Leu Phe Pro Ala Asp Ser Glu His Asn Lys
            275                 280                 285
Leu Lys Ala Ser Gln Ala Arg Asp Leu Leu Ser Lys Met Leu Val Ile
    290                 295                 300
Asp Pro Ala Lys Arg Ile Ser Val Asp Asp Ala Leu Gln His Pro Tyr
305                 310                 315                 320
Ile Asn Val Trp Tyr Asp Pro Ala Glu Val Glu Ala Pro Pro Pro Gln
                325                 330                 335
Ile Tyr Asp Lys Gln Leu Asp Glu Arg Glu His Thr Ile Glu Glu Trp
            340                 345                 350
Lys Glu Leu Ile Tyr Lys Glu Val Met Asn Ser Glu Lys Thr Lys
            355                 360                 365
Asn Gly Val Val Lys Gly Gln Pro Ser Pro Ser Gly Ala Ala Val Asn
    370                 375                 380
Ser Ser Glu Ser Leu Pro Pro Ser Ser Val Asn Asp Ile Ser Ser
385                 390                 395                 400
Met Ser Thr Asp Gln Thr Leu Ala Ser Asp Thr Asp Ser Ser Leu Glu
                405                 410                 415
Ala Ser Ala Gly Pro Leu Gly Cys Cys Arg
                420                 425

(2) INFORMATION FOR SEQ ID NO:4:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Ser Lys Ser Lys Val Asp Asn Gln Phe Tyr Ser Val Glu Val Gly
1               5                   10                  15
Asp Ser Thr Phe Thr Val Leu Lys Arg Tyr Gln Asn Leu Lys Pro Ile
                20                  25                  30
Gly Ser Gly Ala Gln Gly Ile Val Cys Ala Ala Tyr Asp Ala Val Leu
            35                  40                  45
Asp Arg Asn Val Ala Ile Lys Lys Leu Ser Arg Pro Phe Gln Asn Gln
        50                  55                  60
Thr His Ala Lys Arg Ala Tyr Arg Glu Leu Val Leu Met Lys Cys Val
65              70                  75                  80
Asn His Lys Asn Ile Ile Ser Leu Leu Asn Val Phe Thr Pro Gln Lys
                85                  90                  95
Thr Leu Glu Glu Phe Gln Asp Val Tyr Leu Val Met Glu Leu Met Asp
            100                 105                 110
Ala Asn Leu Cys Gln Val Ile Gln Met Glu Leu Asp His Glu Arg Met
        115                 120                 125
```

```
Ser Tyr Leu Leu Tyr Gln Met Leu Ser Ala Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Met Val Arg His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Asn Tyr Val Glu Asn Arg Pro Lys Tyr Ala Gly Leu Thr Phe Pro
                260                 265                 270

Lys Leu Phe Pro Asp Ser Leu Phe Pro Ala Asp Ser Glu His Asn Lys
            275                 280                 285

Leu Lys Ala Ser Gln Ala Arg Asp Leu Leu Ser Lys Met Leu Val Ile
    290                 295                 300

Asp Pro Ala Lys Arg Ile Ser Val Asp Asp Ala Leu Gln His Pro Tyr
305                 310                 315                 320

Ile Asn Val Trp Tyr Asp Pro Ala Glu Val Glu Ala Pro Pro Pro Gln
                325                 330                 335

Ile Tyr Asp Lys Gln Leu Asp Glu Arg Glu His Thr Ile Glu Glu Trp
                340                 345                 350

Lys Glu Leu Ile Tyr Lys Glu Val Met Asn Ser Glu Glu Lys Thr Lys
            355                 360                 365

Asn Gly Val Val Lys Gly Gln Pro Ser Pro Ser Xaa Xaa Gly Ala Ala
        370                 375                 380

Val
385

(2) INFORMATION FOR SEQ ID NO:5:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Ser Arg Ser Lys Arg Asp Asn Asn Phe Tyr Ser Val Glu Ile Ala
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80
```

```
Asn His Lys Asn Ile Ile Gly Leu Leu Asn Val Phe Thr Pro Gln Lys
            85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
            115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
            165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
            195                 200                 205

Trp Ser Val Gly Cys Ile Met Gly Glu Met Val Cys Leu Lys Ile Leu
            210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
            245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
            325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Gly Ala Ala Val Ile
370                 375                 380

Asn Gly Ser Gln His Pro Val Ser Ser Pro Ser Val Asn Asp Met Ser
385                 390                 395                 400

Ser Met Ser Thr Asp Pro Thr Leu Ala Ser Asp
            405                 410
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Ser Asp Ala Ala Val Ser Ser Lys Ala Thr Pro Ser Gln Ser Ser Ser
1               5                   10                  15
```

Ile (2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Gly Ala Ala Val Asn Ser Ser Glu Ser Leu Pro Pro Ser Ser Ser Val
1               5                   10                  15

Gln Pro Ser Pro Ser
            20
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Ser Pro Leu Gly Ala Ala Val Ile Asn Gln Ser Gln His Pro Val Ser
1               5                   10                  15

Ser Pro Ser Val
            20
```

(2) INFORMATION FOR SEQ ID NO:9:

(i) SEQUENCE CHARACTERISTICS:
        (A) LENGTH: 2629 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGATTCCTGT ATGACACTAC ATCATGAGTG ACAGTAAAAG CGATGGCCAG TTTTACAGTG      60

TGCAAGTGGC AGACTCAACT TTCACTGTTC TAAAACGTTA CCAGCAGTTG AAACCAATTG     120

GCTCTGGAGC CCAAGGAATT GTTTGTGCTG CTTTTGATAC AGTTCTTGGA ATAAATGTTG     180

CTGTCAAGAA GTTAAGTCGT CCTTTTCAGA ACCAAACGCA TGCAAAGAGA GCCTACCGTG     240

AACTTGTCCT CCTAAAGTGT GTCAATCATA AAAATATAAT TAGCTTGTTA AATGTGTTCA     300

CACCACAAAA AACGCTAGAA GAATTCCAAG ATGTGTACTT GGTTATGGAG TTAATGGACG     360

CTAACTTATG TCAGGTTATT CATATGGAGC TGGACCATGA AGAATGTCA  TACCTCCTCT     420

ACCAGATGCT TTGTGGCATT AAGCACCTGC ATTCAGCTGG CATAATTCAT AGGGATTTGA     480

AGCCTAGCAA CATTGTAGTA AAATCAGACT GTACTCTCAA GATCCTTGAC TTTGGCCTGG     540

CACGGACAGC CTGTACCAAC TTTATGATGA CTCCCTATGT GGTAACTCGC TACTATCGGG     600

CTCCAGAAGT CATCCTGGGC ATGGGCTACA AGGAGAATGT GGACATCTGG TCTGTCGGGT     660

GCATCATGGC AGAAATGGTC CTCCATAAAT CCTGTTCCCC AGGAAGAGAC TATATTGATC     720

AATGGAATAA AGTTATTGAA CAGCTAGGAA CACCATCCGC AGAGTTCATG AAGAAACTTC     780
```

-continued

```
AGCCAACTGT AAGGAATTAT GTGGAAAACA GACCAAAGTA CCCTGGAATC AAATTTGAAG      840

AGCTCTTTCC AGATTGGATA TTTCCGTCAG AATCCGAACG AGACAAAATA AAAACAAGTC      900

AAGCCAGAGA TCTGTTATCG AAAATGTTAG TGATTGATCC GGACAAGCGG ATCTCTGTGG      960

ACGAAGCCTT GCGCCACCCG TATATTACTG TTTGGTATGA CCCCGCTGAA GCAGAAGCGC     1020

CACCACCTCA AATTTATGAT GCCCAGTTGG AAGAAAGAGA GCATGCGATT GAAGAGTGGA     1080

AAGAACTAAT TTACAAAGAA GTGATGGACT GGGAAGAAAG AAGCAAGAAT GGGGTGAAAG     1140

ACCAGCCTTC AGATGCAGCA GTAAGCAGCA AGGCTACTCC TTCTCAGTCG TCATCCATCA     1200

ATGACATCTC ATCCATGTCC ACTGAGCACA CCCTGGCCTC AGACACAGAC AGCAGTCTCG     1260

ATGCCTCAAC CGGACCCCTG GAAGGCTGCC GATGAAACCT CGCAGATGGC GCACTTGTCT     1320

GTGAAGGACT CTGGCTTCCA TGGCCCTGAG CACATGGGAG CTGGTGGAAC AAATCAAGAA     1380

GCTCCATGTT CTGCATGTAA GAAACACGAC GCCTTGCCCC CACTCAGTTC CAGTAGGATT     1440

GCCTGCGTAG ACTGTAACAT GAGGCAGACG ATGTCTGGAG AAAAAGTACA AACCACACTG     1500

TTAGAAATTT TGTTCAAGAT CATTCAGGTG AGCAATTAGA ATAGCCGAGT TCTTTTCAAG     1560

TCGTGTGGTG TCCTTGGTGA CAGATCATGT GTAACTGTGG GGACTCGTAT GCATGTGACC     1620

ACAAATGCTT GCTTGAACTT GCCCATGTAG CACTTTGGGA ATCAGTATTT AAATGCCAAA     1680

TAATCTTCCA GGTAGTTCTG CTTCTAGAAT AATCTCTTAA TCCTCTTTAG TAATTTGGTG     1740

TCTGTCCACA AAAAAATAGA TTATGTGTGT ATGAATTGGC CACTATCATA TTATCATATT     1800

TTACCCACTT TTATGGTATG ATTTATTCTG TCTTTTGTAT TTCAGAAGGA ATATAATTAA     1860

ATTTATTTAA TAAATAAAAC TACAGCTTTT CTTAAATTTG TGATGTTTTA GGCTGAGAAT     1920

TACCACTGCT TTATATCGAC ACTCTGTGTC CTTTAAACTG CCCACTATGG GAAACTTTAC     1980

GTACAGCTTT CTGCATGACA AAGTTCCAAG TTGTATTTCA CTCTGCTTAA CGACTTATGT     2040

CACCTTGAAT CCTGACCACA CATTTCCTTT TTCTTGGTCC TCTGAACTTG GATCTAGAAT     2100

CCCTCACAGA ACTTCACCTT CTTTATCACA AAGCACCCCA TCTCAGTAGA ATGAATCGGC     2160

AGATTCCTGA GCCCCGCTGC CTAATGTAGA GCTGACAGGG TGGCTTCCCC AGAACGGTGG     2220

GTGGGTGCAT CCTTCCCTGA GCCCACCCAT CCTTTGCTCC CCTCTCTTTA TTTAAGGTGA     2280

AAGGTGATTG GGTCTCATAG CCTTTCCTTT TGTAGCATTG CCTAACTTGT CTTTCTCACT     2340

GACAGAAGCC ACCACGTCCA GCCAGAGCAC ATGGTCTCTT AGGAGACCGG GCTTACTTAC     2400

CATGCATGTT TGCTGCTGTC CTTTTCCATT TTGTGGAGGC ATTTCCTTTT TCTAAGGGAA     2460

TTCCTCAGAT GTTCTAGAAA CATTCAGAAG AACGCAGAAG AAATATTCTA GAGAATTGGG     2520

GGTTCATTCT TGAATATTTT CTGATTTAAA ACTGCTCACC TGAAATTGAT ACTTTCAGAT     2580

CCTGATCTTG TAAATTACTC GAGATTTGGT AAGATGCTGA GTTCTCTGT               2629
```

(2) INFORMATION FOR SEQ ID NO:10:

(i) SEQUENCE CHARACTERISTICS:
        (A) LENGTH: 2629 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GGATTCCTGT ATGACACTAC ATCATGAGTG ACAGTAAAAG CGATGGCCAG TTTTACAGTG       60

TGCAAGTGGC AGACTCAACT TTCACTGTTC TAAAACGTTA CCAGCAGTTG AAACCAATTG      120
```

```
GCTCTGGAGC CCAAGGAATT GTTTGTGCTG CTTTTGATAC AGTTCTTGGA ATAAATGTTG    180

CTGTCAAGAA GTTAAGTCGT CCTTTTCAGA ACCAAACGCA TGCAAAGAGA GCCTACCGTG    240

AACTTGTCCT CCTAAAGTGT GTCAATCATA AAAATATAAT TAGCTTGTTA AATGTGTTCA    300

CACCACAAAA AACGCTAGAA GAATTCCAAG ATGTGTACTT GGTTATGGAG TTAATGGACG    360

CTAACTTATG TCAGGTTATT CATATGGAGC TGGACCATGA AAGAATGTCA TACCTCCTCT    420

ACCAGATGCT TTGTGGCATT AAGCACCTGC ATTCAGCTGG CATAATTCAT AGGGATTTGA    480

AGCCTAGCAA CATTGTAGTA AAATCAGACT GTACTCTCAA GATCCTTGAC TTTGGCCTGG    540

CACGGACAGC CTGTACCAAC TTTATGATGA CTCCCTATGT GGTAACTCGC TACTATCGGG    600

CTCCAGAAGT CATCCTGGGC ATGGGCTACA AGGAGAATGT TGATATCTGG TCAGTGGGTT    660

GCATCATGGG AGAGCTGGTG AAAGGTTGTG TGATATTCCA AGGTACTGAC CATATTGATC    720

AATGGAATAA AGTTATTGAA CAGCTAGGAA CACCATCCGC AGAGTTCATG AAGAAACTTC    780

AGCCAACTGT AAGGAATTAT GTGGAAAACA GACCAAAGTA CCCTGGAATC AAATTTGAAG    840

AGCTCTTTCC AGATTGGATA TTTCCGTCAG AATCCGAACG AGACAAAATA AAAACAAGTC    900

AAGCCAGAGA TCTGTTATCG AAAATGTTAG TGATTGATCC GGACAAGCGG ATCTCTGTGG    960

ACGAAGCCTT GCGCCACCCG TATATTACTG TTTGGTATGA CCCCGCTGAA GCAGAAGCGC   1020

CACCACCTCA AATTTATGAT GCCCAGTTGG AAGAAAGAGA GCATGCGATT GAAGAGTGGA   1080

AAGAACTAAT TTACAAAGAA GTGATGGACT GGGAAGAAAG AAGCAAGAAT GGGGTGAAAG   1140

ACCAGCCTTC AGATGCAGCA GTAAGCAGCA AGGCTACTCC TTCTCAGTCG TCATCCATCA   1200

ATGACATCTC ATCCATGTCC ACTGAGCACA CCCTGGCCTC AGACACAGAC AGCAGTCTCG   1260

ATGCCTCAAC CGGACCCCTG GAAGGCTGCC GATGAAACCT CGCAGATGGC GCACTTGTCT   1320

GTGAAGGACT CTGGCTTCCA TGGCCCTGAG CACATGGGAG CTGGTGGAAC AAATCAAGAA   1380

GCTCCATGTT CTGCATGTAA GAAACACGAC GCCTTGCCCC CACTCAGTTC CAGTAGGATT   1440

GCCTGCGTAG ACTGTAACAT GAGGCAGACG ATGTCTGGAG AAAAAGTACA AACCACACTG   1500

TTAGAAATTT TGTTCAAGAT CATTCAGGTG AGCAATTAGA ATAGCCGAGT TCTTTTCAAG   1560

TCGTGTGGTG TCCTTGGTGA CAGATCATGT GTAACTGTGG GGACTCGTAT GCATGTGACC   1620

ACAAATGCTT GCTTGAACTT GCCCATGTAG CACTTTGGGA ATCAGTATTT AAATGCCAAA   1680

TAATCTTCCA GGTAGTTCTG CTTCTAGAAT AATCTCTTAA TCCTCTTTAG TAATTTGGTG   1740

TCTGTCCACA AAAAAATAGA TTATGTGTGT ATGAATTGGC CACTATCATA TTATCATATT   1800

TTACCCACTT TTATGGTATG ATTTATTCTG TCTTTTGTAT TTCAGAAGGA ATATAATTAA   1860

ATTTATTTAA TAAATAAAAC TACAGCTTTT CTTAAATTTG TGATGTTTTA GGCTGAGAAT   1920

TACCACTGCT TTATATCGAC ACTCTGTGTC CTTTAAACTG CCCACTATGG GAAACTTTAC   1980

GTACAGCTTT CTGCATGACA AAGTTCCAAG TTGTATTTCA CTCTGCTTAA CGACTTATGT   2040

CACCTTGAAT CCTGACCACA CATTTCCTTT TTCTTGGTCC TCTGAACTTG GATCTAGAAT   2100

CCCTCACAGA ACTTCACCTT CTTTATCACA AAGCACCCCA TCTCAGTAGA ATGAATCGGC   2160

AGATTCCTGA GCCCCGCTGC CTAATGTAGA GCTGACAGGG TGGCTTCCCC AGAACGGTGG   2220

GTGGGTGCAT CCTTCCCTGA GCCCACCCAT CCTTTGCTCC CCTCTCTTTA TTTAAGGTGA   2280

AAGGTGATTG GGTCTCATAG CCTTTCCTTT TGTAGCATTG CCTAACTTGT CTTTCTCACT   2340

GACAGAAGCC ACCACGTCCA GCCAGAGCAC ATGGTCTCTT AGGAGACCGG GCTTACTTAC   2400

CATGCATGTT TGCTGCTGTC CTTTTCCATT TTGTGGAGGC ATTTCCTTTT TCTAAGGGAA   2460

TTCCTCAGAT GTTCTAGAAA CATTCAGAAG AACGCAGAAG AAATATTCTA GAGAATTGGG   2520
```

```
GGTTCATTCT TGAATATTTT CTGATTTAAA ACTGCTCACC TGAAATTGAT ACTTTCAGAT    2580

CCTGATCTTG TAAATTACTC GAGATTTGGT AAGATGCTGA GTTCTCTGT               2629
```

(2) INFORMATION FOR SEQ ID NO:11:

(i) SEQUENCE CHARACTERISTICS:
        (A) LENGTH: 1975 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CCCTCCTTAT TCCGGTTTGG AATGTGGCTA ATGAAAGCCC AGTAGGAGGA TTTCTGGGGC      60

AAACAGGTGG ACCAGGATCC TGGTTCTCAG GCACGGAATG GCTATTGTGA GAGCGCCACC     120

AGCAGGACCA TCGCAGATCT TGGTTATGGC TGCTCACGCA AGAGGCTGTT GATGTAGACC     180

CCCTTTCCCG TAGATGAGAA ATCACACGAG CAGTGGTATT TATGAGCCTC CATTTCTTAT     240

ACTACTGCAG TGAACCAACC TTGGATGTGA AAATTGCCTT TTGTCAGGTG TGTGTTCCTT     300

ACAGGTAAAA CAAAGGGATT CGACAAACAC GTGGATGTGT CTTCTGTTGT CAAACATTAC     360

AACATGAGCA AAGCAAGGT AGATAACCAG TTCTACAGTG TGGAAGTGGG AGACTCAACC      420

TTCACAGTTC TAAAGCGCTA CCAGAACCTG AAGCCGATCG GCTCTGGGGC TCAGGGAATA     480

GTTTGTGCTG CGTATGACGC TGTCCTCGAC AGAAATGTGG CCATTAAGAA GCTCAGCAGA     540

CCCTTCCAGA ACCAAACTCA TGCCAAGAGG GCTTACCGGG AGCTGGTCCT CATGAAGTGT     600

GTGAACCATA AAAACATTAT TAGCTTATTA AATGTCTTTA CACCCCAGAA AACACTGGAG     660

GAGTTCCAAG ATGTTTACTT AGTGATGGAA CTGATGGACG CCAACTTGTG TCAGGTGATT     720

CAGATGGAGC TGGACCACGA GCGGATGTCG TACTTGCTGT ACCAGATGCT GTCGGCGATC     780

AAACACCTCC ACTCCGCTGG GATCATCCAC AGGGACTTAA AACCCAGTAA CATCGTAGTC     840

AAGTCTGATT GCACACTGAA AATCCTGGAC TTTGGACTGG CCAGGACAGC GGGCACAAGC     900

TTCATGATGA CTCCGTATGT GGTGACGAGA TATTACAGAG CCCCCGAGGT CATCCTGGGC     960

ATGGGCTACA AGGAGAACGT GGACATATGG TCTGTGGGCT GCATCATGGG AGAAATGGTT    1020

CGTCACAAAA TCCTCTTTCC CGGAAGGGAC TATATTGACC AGTGGAACAA AGTCATAGAG    1080

CAGCTAGGAA CTCCGTGTCC AGAATTCATG AAGAAATTGC AGCCCACCGT CAGAAACTAC    1140

GTGGAGAACC GGCCCAAGTA TGCAGGCCTC ACCTTCCCCA AGCTCTTTCC AGATTCCCTC    1200

TTCCCAGCGG ATTCCGAGCA CAATAAACTT AAAGCCAGCC AAGCCAGGGA CTTGTTGTCA    1260

AAGATGTTAG TGATTGACCC AGCGAAGAGG ATATCGGTGG ATGACGCATT GCAGCATCCG    1320

TACATCAACG TTTGGTACGA CCCTGCTGAA GTGGAGGCGC CTCCGCCTCA GATATATGAC    1380

AAGCAATTGG ATGAAAGGGA GCACACCATC GAAGAATGGA AGAACTCAT CTACAAGGAA     1440

GTAATGAACT CAGAAGAGAA GACTAAGAAC GGCGTAGTCA AAGGCCAGCC CTCACCTTCA    1500

GGTGCAGCAG TGAACAGCAG TGAGAGTCTC CCTCCATCCT CATCTGTCAA CGACATCTCC    1560

TCCATGTCCA CCGACCAGAC CCTCGCATCC GACACTGACA GCAGCCTGGA AGCCTCGGCG    1620

GGACCGCTGG GTTGTTGCAG GTGACTAGCC GCCTGCCTGC GAAACCCAGC GTTCTTCAGG    1680

AGATGACGCC ATGATAGAAC ACAGCGCACA TGCACACACA CAGAGCTTGT ACACACACAC    1740

ACACACACAC ACACACGCAC GCACGCACGC ACGCAAGCAC GCACGCACGC ACAAATGCAC    1800

TCACGCAATG TCAAGAAAAA AAAAAGTAGC GAGAGAGAGC GAGAGAGCCA ACGTAAAACT    1860
```

-continued

```
AAGTTAAATC TTTCTGCGTG CTTCTCCAGA GTTCTGTATC GCAGCTGAGC TGAAATGTAT   1920

ACTTAACTTC TAGTCGCGCT CGCTCGACTT TGGTCTCCCT CCGGCAGTGC TTACT        1975
```

(2) INFORMATION FOR SEQ ID NO:12:

(i) SEQUENCE CHARACTERISTICS:
        (A) LENGTH: 1986 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
CCCTATCCCT CCTTATTCCG GTTTGGAATG TGGCTAATGA AAGCCCAGTA GGAGGATTTC     60

TGGGGCAAAC AGGTGGACCA GGATCCTGGT TCTCAGGCAC GGAATGGCTA TTGTGAGAGC    120

GCCACCAGCA GGACCATCGC AGATCTTGGT TATGGCTGCT CACGCAAGAG GCTGTTGATG    180

TAGACCCCCT TTCCCGTAGA TGAGAAATCA CACGAGCAGT GGTATTTATG AGCCTCCATT    240

TCTTATACTA CTGCAGTGAA CCAACCTTGG ATGTGAAAAT TGCCTTTTGT CAGGTGTGTG    300

TTCCTTACAG GTAAAACAAA GGGATTCGAC AAACACGTGG ATGTGTCTTC TGTTGTCAAA    360

CATTACAACA TGAGCAAAAG CAAGGTAGAT AACCAGTTCT ACAGTGTGGA AGTGGGAGAC    420

TCAACCTTCA CAGTTCTAAA GCGCTACCAG AACCTGAAGC CGATCGGCTC TGGGGCTCAG    480

GGAATAGTTT GTGCTGCGTA TGACGCTGTC CTCGACAGAA ATGTGGCCAT TAAGAAGCTC    540

AGCAGACCCT TCCAGAACCA AACTCATGCC AAGAGGGCTT ACCGGGAGCT GGTCCTCATG    600

AAGTGTGTGA ACCATAAAAA CATTATTAGC TTATTAAATG TCTTTACACC CCAGAAAACA    660

CTGGAGGAGT TCCAAGATGT TTACTTAGTG ATGGAACTGA TGGACGCCAA CTTGTGTCAG    720

GTGATTCAGA TGGAGCTGGA CCACGAGCGG ATGTCGTACT TGCTGTACCA GATGCTGTCG    780

GCGATCAAAC ACCTCCACTC CGCTGGGATC ATCCACAGGG ACTTAAAACC CAGTAACATC    840

GTAGTCAAGT CTGATTGCAC ACTGAAAATC CTGGACTTTG GACTGGCCAG ACAGCGGGC     900

ACAAGCTTCA TGATGACTCC GTATGTGGTG ACGAGATATT ACAGAGCCCC CGAGGTCATC    960

CTGGGCATGG GCTACAAGGA GAACGTGGAC ATATGGTCTG TGGGCTGCAT CATGGGAGAA   1020

ATGGTTCGTC ACAAAATCCT CTTTCCCGGA AGGGACTATA TTGACCAGTG GAACAAAGTC   1080

ATAGAGCAGC TAGGAACTCC GTGTCCAGAA TTCATGAAGA AATTGCAGCC CACCGTCAGA   1140

AACTACGTGG AGAACCGGCC CAAGTATGCA GGCCTCACCT TCCCCAAGCT CTTTCCAGAT   1200

TCCCTCTTCC CAGCGGATTC CGAGCACAAT AAACTTAAAG CCAGCCAAGC CAGGGACTTG   1260

TTGTCAAAGA TGTTAGTGAT TGACCCAGCG AAGAGGATAT CGGTGGATGA CGCATTGCAG   1320

CATCCGTACA TCAACGTTTG GTACGACCCT GCTGAAGTGG AGGCGCCTCC GCCTCAGATA   1380

TATGACAAGC AATTGGATGA AAGGGAGCAC ACCATCGAAG AATGGAAAGA ACTCATCTAC   1440

AAGGAAGTAA TGAACTCAGA AGAGAAGACT AAGAACGGCG TAGTCAAAGG CCAGCCCTCA   1500

CCTTCAGCAC AGGTGCAGCA GTGAACAGCA GTGAGAGTCT CCCTCCATCC TCATCTGTCA   1560

ACGACATCTC CTCCATGTCC ACCGACCAGA CCCTCGCATC CGACACTGAC AGCAGCCTGG   1620

AAGCCTCGGC GGGACCGCTG GGTTGTTGCA GGTGACTAGC CGCCTGCCTG CGAAACCCAG   1680

CGTTCTTCAG GAGATGACGC CATGATAGAA CACAGCGCAC ATGCACACAC ACAGAGCTTG   1740

TACACACACA CACACACACA CACACACGCA CGCACGCACG CACGCAAGCA CGCACGCACG   1800

CACAAATGCA CTCACGCAAT GTCAAGAAAA AAAAAAGTAG CGAGAGAGAG CGAGAGAGCC   1860
```

```
AACGTAAAAC TAAGTTAAAT CTTTCTGCGT GCTTCTCCAG AGTTCTGTAT CGCAGCTGAG    1920

CTGAAATGTA TACTTAACTT CTAGTCGCGC TCGCTCGACT TTGGTCTCCC TCCGGCAGTG    1980

CTTACT                                                               1986

(2) INFORMATION FOR SEQ ID NO:13:

(i) SEQUENCE CHARACTERISTICS:
         (A) LENGTH: 1408 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:13:

GCGGCCGAGC GCGGGACGTT GCGGCCGAAA CGCGGAGCCG CGAGCAGGAT TAAGTAGCGG      60

CCCGGCCACC GGCACGGCGC CGCTCTCCGC TACTGGCTTC CAGGTCTCCG TTGGCTGCAC     120

TGCCGGCCGG TTGTTGAATA TTTGGATGAA GCCATTAGAC TAATTGCTTG CCATCATGAG     180

CAGAAGTAAA CGTGACAACA ATTTTTATAG TGTAGAGATC GCAGATTCTA CATTCACAGT     240

CCTAAAACGA TACCAGAACT TAAAGCCTAT AGGCTCAGGA GCTCAAGGAA TAGTGTGTGC     300

AGCTTATGAT GCTATTCTTG AAAGAAATGT TGCAATCAAG AAGCTCAGCC GGCCATTTCA     360

GAATCAGACC CATGCTAAGC GAGCCTACCG AGAACTAGTT CTTATGAAGT GTGTTAATCA     420

CAAAATATA ATTGGCCTTT TGAATGTTTT CACACCACAG AAATCCCTAG AAGAATTTCA      480

AGATGTTTAC ATAGTCATGG AGCTCATGGA TGCAAATCTT TGCCAAGTGA TTCAGATGGA     540

GTTAGATCAT GAAAGAATGT CCTACCTTCT CTATCAAATG CTGTGTGGAA TCAAGCACCT     600

TCACTCTGCT GGAATTATTC ATCGGGACTT AAAGCCTAGT AATATAGTAG TCAAATCAGA     660

CTGCACTTTG AAGATTCTTG ATTTTGGACT GGCAAGGACT GCAGGAACGA GTTTTATGAT     720

GACGCCTTAC GTGGTAACTC GTTACTACAG AGCACCAGAG GTCATTCTCG GCATGGGCTA     780

CAAGGAGAAC GTGGATTTAT GGTCTGTGGG GTGCATTATG GGAGAAATGG TTTGCCTCAA     840

AATCCTCTTT CCAGGAAGGG ACTATATTGA TCAGTGGAAT AAAGTTATTG AACAGCTCGG     900

AACACCTTGT CCTGAATTCA TGAAGAAACT ACAACCAACA GTAAGGACTT ACGTTGAAAA     960

CAGACCTAAG TACGCTGGCT ATAGCTTTGA GAAACTGTTT CCTGATGTGC TTTTCCCAGC    1020

TGACTCAGAA CATAACAAAC TTAAAGCCAG TCAGGCGAGA GATTTGTTAT CTAAAATGCT    1080

GGTGATAGAT GCGTCCAAAA GGATCTCCGT AGACGAAGCT CTCCAGCACC CGTACATCAA    1140

CGTCTGGTAT GATCCTTCAG AAGCAGAGGC CCCACCACCA AAGATCCCTG ACAAGCAGTT    1200

AGATGAAAGG GAGCACACAA TAGAGGAGTG GAAAGAACTG ATATACAAGG AGGTCATGGA    1260

TTTGGAGGAG CGAACTAAGA ATGGCGTCAT AAGAGGGCAG CCGTCTCCTT TAGGTGCAGC    1320

AGTGATCAAT GGCTCTCAGC ATCCGGTCTC TTCGCCGTCT GTCAATGACA TGTCTTCAAT    1380

GTCCACAGAT CCGACTCTGG CCTCGGAT                                      1408

(2) INFORMATION FOR SEQ ID NO:14:

(i) SEQUENCE CHARACTERISTICS:
         (A) LENGTH: 51 base pairs
         (B) TYPE: nucleic acid
         (C) STRANDEDNESS: single
         (D) TOPOLOGY: linear (ii) MOLECULE TYPE: cDNA
```

```
        (xi) SEQUENCE DESCRIPTION: SEQ ID NO:14:

TCAGATGCAG CAGTAAGCAG CAAGGCTACT CCTTCTCAGT CGTCATCCAT C            51

(2) INFORMATION FOR SEQ ID NO:15:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CAGCCCTCAC CTTCAGGTGC AGCAGTGAAC AGCAGTGAGA GTCTCCCTCC ATCCTCATCT    60

GTC                                                                 63

(2) INFORMATION FOR SEQ ID NO:16:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TCTCCTTTAG GTGCAGCAGT GATCAATGGC TCTCAGCATC CGGTCTCTTC GCCGTCTGTC    60
```